(12) United States Patent
Wu et al.

(10) Patent No.: US 10,395,918 B2
(45) Date of Patent: Aug. 27, 2019

(54) METHOD AND SYSTEM FOR CONTROLLING PLASMA IN SEMICONDUCTOR FABRICATION

(71) Applicant: TAIWAN SEMICONDUCTOR MANUFACTURING CO., LTD., Hsin-Chu (TW)

(72) Inventors: Cheng-Tsung Wu, Zhubei (TW); Po-Hsiung Leu, Taoyuan (TW); Ding-I Liu, Hsinchu (TW); Si-Wen Liao, Hsinchu (TW); Hsiang-Sheng Kung, Zhubei (TW)

(73) Assignee: TAIWAN SEMICONDUCTOR MANUFACTURING CO., LTD., Hsin-Chu (TW)

(*) Notice: Subject to any disclaimer, the term of this patent is extended or adjusted under 35 U.S.C. 154(b) by 0 days.

(21) Appl. No.: 14/836,574

(22) Filed: Aug. 26, 2015

(65) Prior Publication Data

US 2016/0343625 A1 Nov. 24, 2016

Related U.S. Application Data (60) Provisional application No. 62/165,477, filed on May 22, 2015.

(51) Int. Cl.
*H01J 37/32* (2006.01)
*H01L 21/02* (2006.01)

(52) U.S. Cl.
CPC .... *H01L 21/02274* (2013.01); *H01J 37/3244* (2013.01); *H01J 37/32357* (2013.01); *H01J 37/32449* (2013.01); *H01J 37/32972* (2013.01)

(58) Field of Classification Search
USPC ..................................................... 427/248.1
See application file for complete search history.

(56) References Cited

U.S. PATENT DOCUMENTS

| | | | |
|---|---|---|---|
| 4,803,365 A * | 2/1989 | Krause | G01N 21/64 250/432 R |
| 6,590,179 B2 * | 7/2003 | Tanaka | H01J 37/32935 216/67 |
| 7,001,482 B2 | 2/2006 | Landis et al. | |

(Continued)

FOREIGN PATENT DOCUMENTS

| CN | 101359586 | 9/2011 |
|---|---|---|
| CN | 101441984 | 10/2011 |

(Continued)

OTHER PUBLICATIONS

Mackus (J. Vac. Sci. Technol. A 28(1),Jan./Feb. 2010,pp. 77-87).*

(Continued)

*Primary Examiner* — Joel G Horning
(74) *Attorney, Agent, or Firm* — Haynes and Boone, LLP (57) ABSTRACT

A plasma processing system and a method for controlling a plasma in semiconductor fabrication are provided. The system includes a remote plasma module configured to generate a plasma. The system further includes a compound mixing member configured to receive the plasma. The system also includes a processing chamber configured to receive the plasma from the compound mixing member for processing. In addition, the system includes a detection module configured to monitor the plasma in the compound mixing member.

20 Claims, 6 Drawing Sheets

(56) References Cited

U.S. PATENT DOCUMENTS

| | | | |
|---|---|---|---|
| 7,129,187 B2 * | 10/2006 | Joe | C23C 16/30 |
| | | | 257/E21.263 |
| 7,790,478 B2 | 9/2010 | Fujii et al. | |
| 8,944,003 B2 | 2/2015 | Chen et al. | |
| 9,312,154 B2 | 4/2016 | Tran et al. | |
| 2002/0036066 A1 | 3/2002 | Ogawa et al. | |
| 2002/0179248 A1 | 12/2002 | Kabansky | |
| 2004/0086434 A1 | 5/2004 | Gadgil et al. | |
| 2006/0068104 A1 | 3/2006 | Ishizaka et al. | |
| 2006/0137612 A1 | 6/2006 | Holber et al. | |
| 2009/0047447 A1 | 2/2009 | Sawin et al. | |
| 2014/0179114 A1 | 6/2014 | van Schravendijk | |

FOREIGN PATENT DOCUMENTS

| | | |
|---|---|---|
| CN | 102203898 | 11/2016 |
| KR | 20050087196 A | 8/2005 |
| TW | 200821402 A | 5/2008 |
| TW | 200948219 A | 11/2009 |
| WO | WO 03/065132 A2 | 8/2003 |

OTHER PUBLICATIONS

Mackus, A. J. M., Heil, S. B. S., Langereis, E., Knoops, H. C. M., Sanden, van de, M. C. M., & Kessels, W. M. M. (2010). Optical emission spectroscopy as a tool for studying, optimizing, and monitoring plasma-assisted atomic layer deposition processes. Journal of Vacuum Science and Technology. A: Vacuum, Surfaces, and Films, 28(1), 77-87. DOI: 10.1116/1.3256227.

* cited by examiner

METHOD AND SYSTEM FOR CONTROLLING PLASMA IN SEMICONDUCTOR FABRICATION

CROSS REFERENCE TO RELATED APPLICATIONS

This application claims priority under 35 U.S.C. 119(e) to U.S. Provisional Application No. 62/165,477, filed on May 22, 2015, all of which are hereby expressly incorporated by reference into the present application.

BACKGROUND

Semiconductor devices are used in a variety of electronic applications, such as personal computers, cell phones, digital cameras, and other electronic equipment. Semiconductor devices are typically fabricated by sequentially depositing insulating or dielectric layers, conductive layers, and semiconductor layers of materials over a semiconductor substrate, and patterning the various material layers using lithography to form an integrated circuit (IC) and elements thereon. ICs in the newer generations have more complex circuits than ICs in the previous generations as technologies advance. However, for these advances to be realized, similar developments in IC processing and manufacturing are needed.

During the manufacturing of semiconductor devices, various processing steps are used to fabricate integrated circuits on a semiconductor wafer. One of the most difficult factors in the continuing evolution toward smaller device sizes and higher circuit density is to consistently form circuits with smaller critical dimensions within predetermined error windows. For example, semiconductor feature sizes are frequently subject to optical or electrical metrology inspections following photolithographic patterning and etching to ensure that critical dimensions are within acceptable limits.

Although existing methods and devices for performing the processing steps have been generally adequate for their intended purposes, they have not been entirely satisfactory in all respects. Consequently, it would be desirable to provide a solution for process control in semiconductor manufacturing operations.

BRIEF DESCRIPTION OF THE DRAWINGS

Aspects of the present disclosure are best understood from the following detailed description when read with the accompanying figures. It should be noted that, in accordance with the standard practice in the industry, various features are not drawn to scale. In fact, the dimensions of the various features may be arbitrarily increased or reduced for clarity of discussion.

DETAILED DESCRIPTION

The following disclosure provides many different embodiments, or examples, for implementing different features of the subject matter provided. Specific examples of solutions and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Furthermore, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. It should be understood that additional operations can be provided before, during, and after the method, and some of the operations described can be replaced or eliminated for other embodiments of the method.

Figure 1:
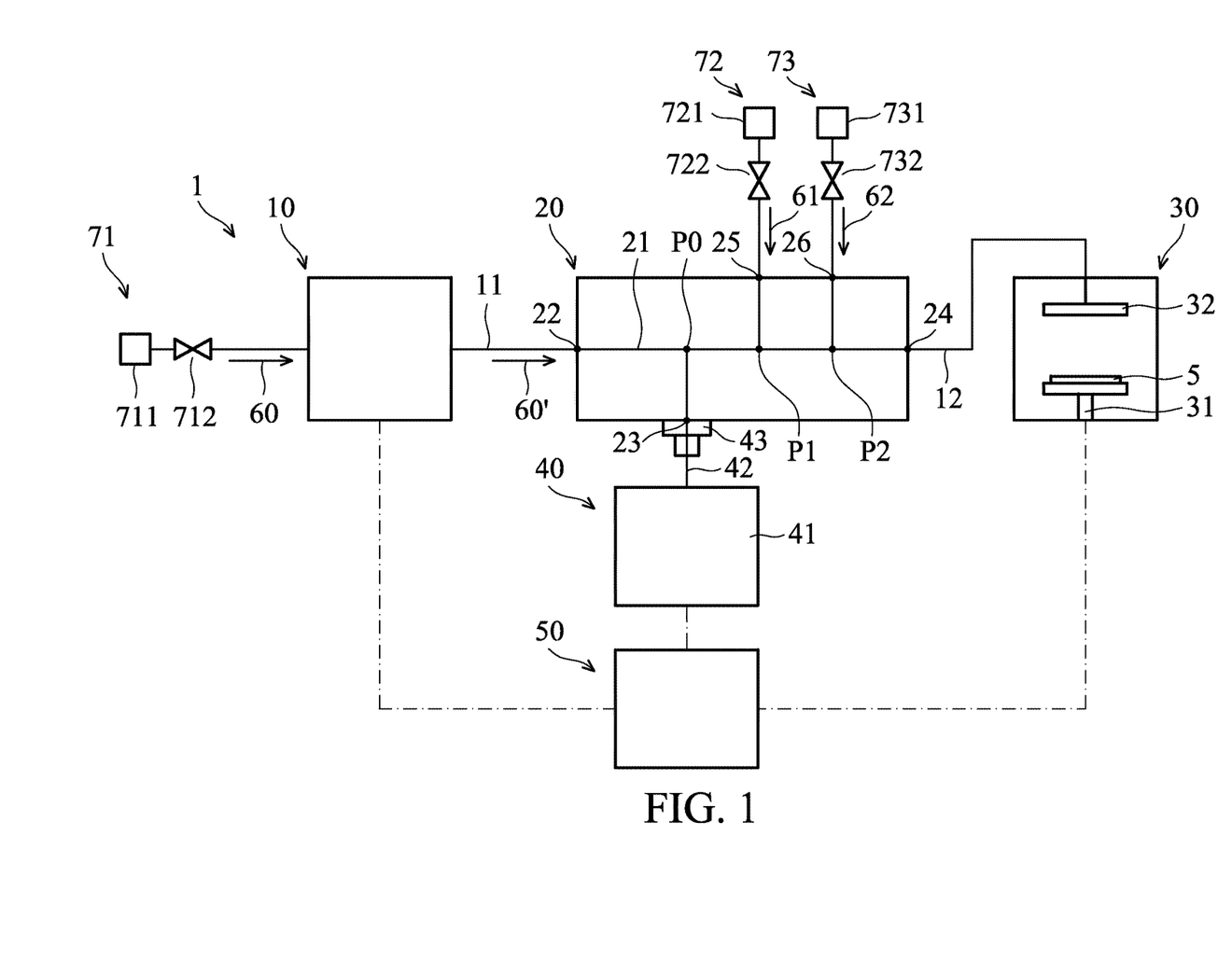
FIG. 1 is a block diagram of a processing system in semiconductor fabrication, in accordance with some embodiments.

FIG. 1 shows a schematic view of a plasma processing system 1, in accordance with some embodiments. The plasma processing system 1 is configured to process one or more wafers 5. The wafer 5 to be processed may include a semiconductor, conductor, and/or insulator layers. In some embodiments, the wafer 5 includes layered semiconductors. Examples include the layering of a semiconductor layer on an insulator such as a silicon-on-insulator (SOI) substrate, a silicon-on-sapphire substrate, or a silicon-germanium-on-insulator substrate, or the layering of a semiconductor on glass to produce a thin film transistor (TFT). The wafer 5 may go through several processing steps, such as lithography, etching, and/or doping, before a completed die is formed.

In some embodiments, the plasma processing system 1 includes a remote plasma module 10, a compound mixing member 20, a processing chamber 30, a detection module 40, a control module 50, a plasma gas supply unit 71, and a number of processing gas supply units 72 and 73. Additional features can be added to the wafer process system, and some of the features described below can be replaced or eliminated in other embodiments of the wafer process system.

The remote plasma module 10 is configured to supply and control at least one plasma to enable process applications in the processing chamber 30. In some embodiments, the remote plasma module 10 includes a power source, a control module, and a plasma chamber. One or more inductive coil elements disposed adjacent to the plasma chamber are coupled to a radio frequency (RF) plasma power source. The plasma source gas (non-plasma phase) 60 from the plasma gas supply unit 71 excited into the plasma 60' when the plasma source gas 60 is supplied into the remote plasma module 10. The remote plasma module 10 further delivers the plasma 60' to the compound mixing member 20. In some embodiments, the remote plasma module 10 supplies and delivers a number of different plasmas to the processing chamber 30.

In some embodiments, the plasma gas supply unit 71 includes a storage tank 711 and a gas controller 712. The storage tank 711 is configured to store a plasma source gas 60 to be delivered to the remote plasma module 10. The plasma source gas 60 may be selected from the group consisting of $O_2$, $H_2O$, $NH_3$, $N_2$, and $H_2$. The gas controller 712 is configured to control the connection and delivery rate of the plasma source gas 60 to the remote plasma module 10. The gas controller 712 may include devices such as valves, flow meters, sensors, and the like. In some embodiments, the gas controller 712 is controlled by and receives instructions from the control module 50.

In some embodiments, the processing gas supply units 72 and 73 include components similar to the plasma gas supply unit 71. For example, the processing gas supply unit 72 includes a storage tank 721 and a gas controller 722. The storage tank 721 is configured to contain a processing gas 61. The gas controller 722 is configured to control the connection and delivery rate of the processing gas 61 to the compound mixing member 20. The processing gas supply unit 73 includes a storage tank 731 and a gas controller 732. The storage tank 731 is configured to contain a processing gas 62. The gas controller 732 is configured to control the connection and delivery rate of the processing gas 62 to the compound mixing member 20.

The processing gas 61 and 62 supplied from the processing gas supply units 72 and 73 may be the same as or different from the plasma source gas 60 supplied from the plasma gas supply unit 71. In some embodiments, the plasma source gas 60 is nitrogen, the processing gas 61 includes Silane ($SiH_4$), and the processing gas 62 includes Tungsten hexafluoride ($WF_6$). In some embodiments, the processing gases 61 and 62 are supplied into the compound mixing member 20 without being turned into plasma as the plasma 60' (i.e., in a non-plasma phase) from the plasma gas supply unit 71.

The compound mixing member 20 is configured to receive gases and plasma from different sources and direct the compound to the processing chamber 30. In some embodiments, the compound mixing member 20 is configured to receive gases and plasma from different sources and mixes all the compounds before they reach the processing chamber 30. In some embodiments, there is no gas supplied into the compound mixing member 20, but one or more different plasmas are supplied to the processing chamber 30 via the compound mixing member 20.

In some embodiments, the compound mixing member 20 includes a flow path 21 formed therein to enable gas or plasma to flow therethrough. In some embodiments, the compound mixing member 20 further includes a number of inlet ports (such as the inlet ports 22, 25 and 26), a viewing window 23, and an outlet port 24. The inlet ports 22, 25 and 26, the viewing window 23, and the outlet port 24 are connected to the flow path 21.

In some embodiments, the compound mixing member 20 is connected to the remote plasma module 10 via the inlet port 22. A gas line 11, as shown in FIG. 1, is connected between the remote plasma module 10 and the inlet port 22 of the compound mixing member 20. In addition, the compound mixing member 20 is connected to the processing chamber 30 via the outlet port 24. A gas line 12, as shown in FIG. 1, is connected between the processing chamber 30 and the outlet port 24 of the compound mixing member 20. The gas lines 11 and 12 may be a tube, a pipe, or a similar device. In some embodiments, the gas lines 11 and 12 are detachably connected to the compound mixing member 20 and fixed on the compound mixing member 20 via suitable means, such as screws. In some embodiments, the inlet port 22 and the outlet port 24 are formed at two ends of the flow path 21.

In some embodiments, the compound mixing member 20 is connected to the processing gas supply unit 72 via the inlet port 25, and the compound mixing member 20 is connected to the processing gas supply unit 73 via the inlet port 26. As shown in FIG. 1, the inlet port 25 is connected to the flow path 21 at an intersection P1, and the inlet port 26 is connected to the flow path 21 at an intersection P2. The intersection P1 is located upstream of the intersection P2. However, it should be appreciated that other variations and modifications can be made to embodiments of the disclosure. In some embodiments, for example, the intersection P1 and the intersection P2 are arranged in the same position.

The viewing window 23 is connected to the flow path 21 for allowing a detection of the plasma 60' before the plasma 60' approaches the intersections P1 and P2. In some embodiments, as shown in FIG. 1, the viewing window 23 is connected to the flow path 21 at an intersection P0. The intersection P0 is located upstream of the intersections P1 and P2. That is, the intersections P1 and P2 are farther away from the inlet port 22 than the intersection P0. As a result, after the plasma 60' is supplied into the compound mixing member 20 via the inlet port 22, the plasma 60' first flows through the intersection P0 then the intersections P1 and P2. Afterwards, the plasma 60' leaves the compound mixing member 20 via the outlet port 24.

Figure 2A:
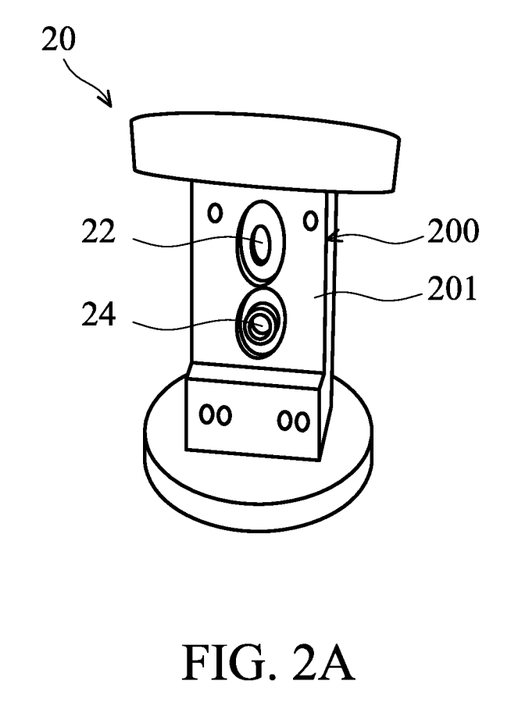
FIG. 2A is a front schematic diagram of a gas mixing member, in accordance with some embodiments.

FIG. 2A shows a front schematic view of the compound mixing member 20, in accordance with some embodiments. In some embodiments, the compound mixing member 20 includes a main body 200. The inlet port 22 and the outlet port 24 are formed on the same outer surface of the main body 200, such as a front surface 201 of the main body 200. The inlet port 22 is formed adjacent to a top end of the main body 200, and the outlet port 24 is formed adjacent to a bottom end of the main body 200.

Figure 2B:
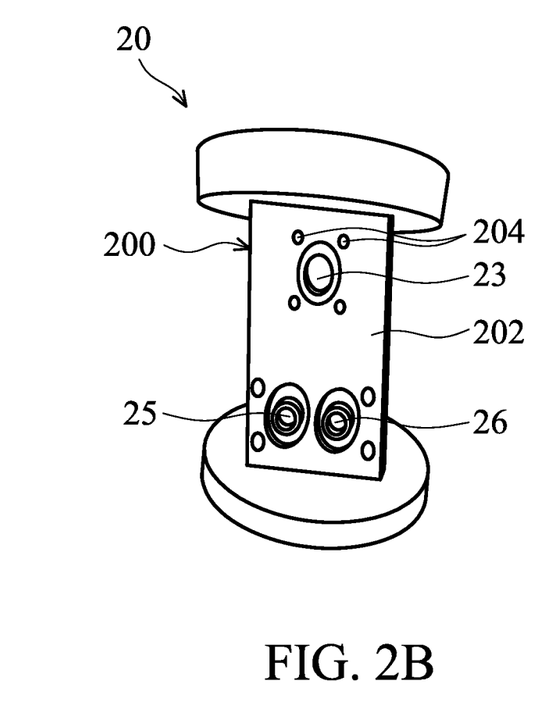
FIG. 2B is a rear schematic diagram of a gas mixing member, in accordance with some embodiments.

FIG. 2B shows a rear schematic view of the compound mixing member 20, in accordance with some embodiments. In some embodiments, the two additional inlet ports 25 and 26 are formed on one of the outer surfaces (such as the rear surface 202) of the main body 200, and the viewing window 23 is also formed on one of the outer surfaces (such as the rear surface 202) of the main body 200. The two additional inlet ports 25 and 26 are formed adjacent to the bottom end of the main body 200, and the viewing window 23 is formed adjacent to the top end of the main body 200. In some embodiments, the inlet port 22 and the viewing window 23 are formed at two opposite outer surfaces of the main body 200. In addition, the inlet port 22 is aligned to the viewing window 23. As a result, the inlet port 22 and the viewing window 23 are arranged along the same axis.

The configuration of the compound mixing member 20 may be varied. In some embodiments, the viewing window 23 is formed on any outer surface of the main body, such as a rear surface 203 or a lateral surface, which connects the front surface 201 to the rear surface 203 of the main body 200.

Referring to FIG. 1, the processing chamber 30 is configured to use the gas from the compound mixing member 20 to process one or more wafers 5. In some embodiments, the processing chamber 30 uses remote plasma (such as the plasma 60') and processing gas(es) (such as the processing gases 61 and 62) to form a deposited layer on a wafer 5 positioned in the processing chamber 30. However, while the embodiment is described with reference to the deposition process, the embodiments are not limited thereto. Rather, any process that utilizes plasma may benefit from the embodiments, such as plasma assisted etching processes, plasma treatment processes, or the like. All such plasma processes and remote plasma processes are fully intended to be included within the scope of the embodiments.

In some embodiments, the processing chamber 30 includes a mounting platform 31 and a showerhead 32. The mounting platform 31, for example, an electrostatic chuck (ESC), is positioned in the disclosure processing chamber 30 for supporting the wafer 5. The mounting platform 31 may be rotatable and may include heating mechanisms in order to heat the substrate 5 during the deposition process. It should be appreciated that while a single mounting platform 31 is illustrated in FIG. 1, any number of mounting platforms 31 may additionally be included within the processing chamber 30.

In some embodiments, the showerhead 32 is configured to receive the gas from the compound mixing member 20 and disperse the gas on in a thin and even distribution around the processing chamber 30. The showerhead 32 may have a circular design with openings dispersed evenly around the showerhead 32. Process conditions such as pressure within the processing chamber 30 may be controlled by a pump.

Figure 3A:
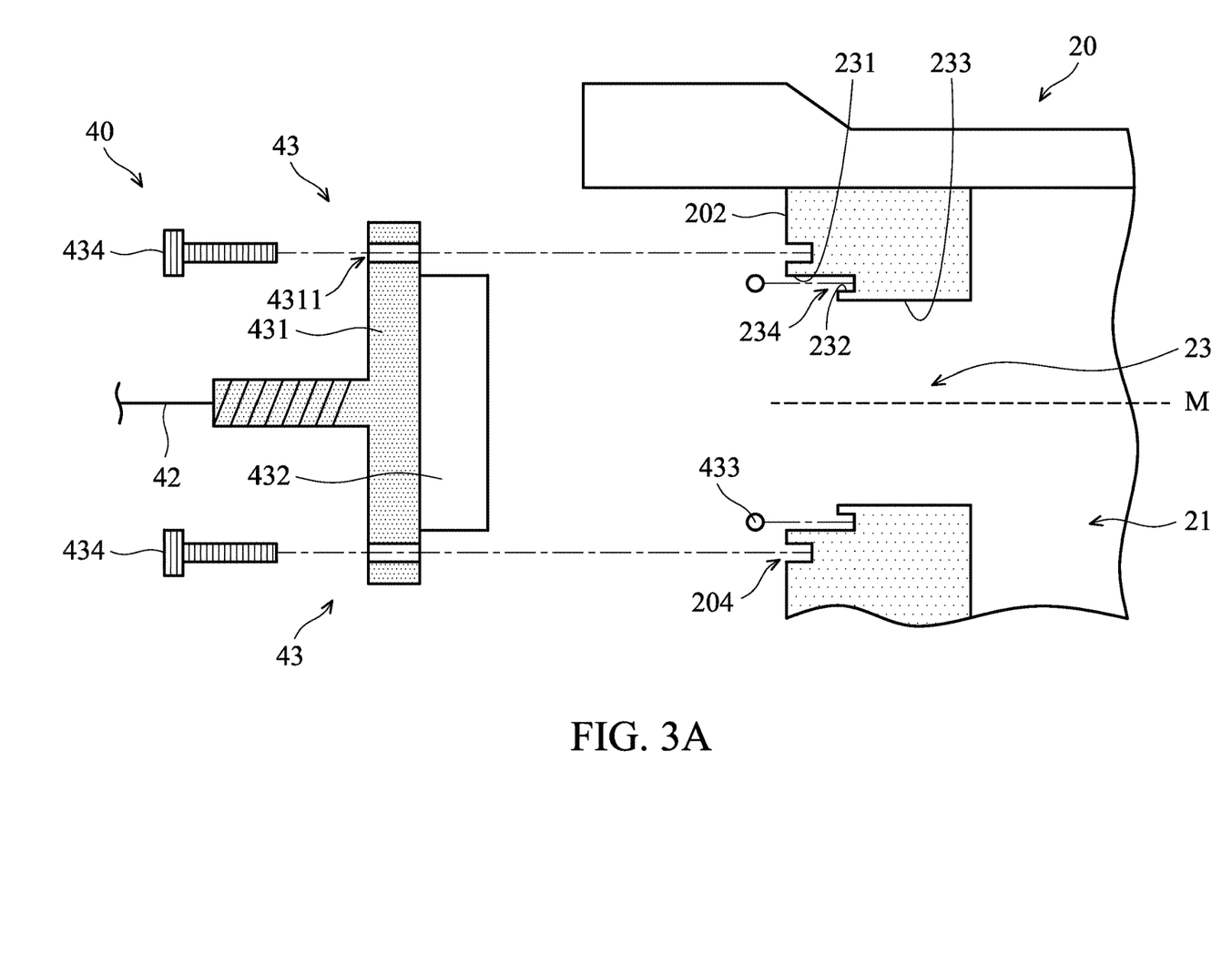
FIG. 3A is an exploded view of a detection module before being mounted on a gas mixing member, in accordance with some embodiments.

FIG. 3A is an exploded view of a detection module before being mounted on a gas mixing member, in accordance with some embodiments. In some embodiments, the detection module 40 is an optical emission spectrometer. However, other variations and modifications can be made to embodiments of the disclosure. In some embodiments, for examples, the detection module 40 includes fixed transmitters and tunable receivers (FTTR). The FTTR is configured for real-time detection of the condition of the plasma 60' in the flow path 21.

The detection module 40 includes a computer 41 (FIG. 1), a signal line 42, and a probing assembly 43, in accordance with some embodiments. The probing assembly 43 is connected to the computer 41 via the signal line 42. The probing assembly 43 includes a spectrophotometer 431, a substrate 432, and a sealing member 433. The spectrophotometer 431 measures a light beam's intensity as a function of its color (wavelength). The spectrophotometer 431 is electrically connected to the signal line 42 and physically connected to the substrate 432. The substrate 432 includes a transparent glass.

The sealing member 433, such as an O-ring, is positioned between a surface of the substrate 432 opposite to the surface where the spectrophotometer 431 is disposed and the compound mixing member 20. Specifically, as shown in FIG. 3A, the viewing window 23 includes a passage extending along a straight axis M. The passage includes a first inner wall 231, a second inner wall 232, and a third inner wall 233. The first inner wall 231 connects the rear surface 202 to the second inner wall 232, and the third inner wall 233 connects the second inner wall 232 to the flow path 21. The first and third inner walls 231 and 233 extend parallel to the straight axis M. The second inner wall 232 is arranged perpendicular to the first and third inner walls 231 and 233. A circular groove 234 is peripherally formed on the second inner wall 232. The sealing member 433 is positioned in the circular groove 234. However, other variations and modifications can be made to embodiments of the disclosure. In some other non-illustrated embodiments, for example, a groove is formed on the substrate 432, and the sealing member 433 is positioned in the groove of the substrate 432.

The assembly sealing member 433 is positioned on the compound mixing member 20, and the probing assembly 43 is positioned corresponding to the viewing window 23 of the compound mixing member 20. In some embodiments, the probing assembly 43 is mounted on the compound mixing member 20 via the spectrophotometer 431 by suitable means. For example, as shown in FIG. 3A, the spectrophotometer 431 is fixed on the rear surface 202 via a number of screws 434. Each of the screws 434 passes through a through hole 4311 formed on the spectrophotometer 431 and mates with a hole 204 with internal thread on the rear surface 202.

Figure 3B:
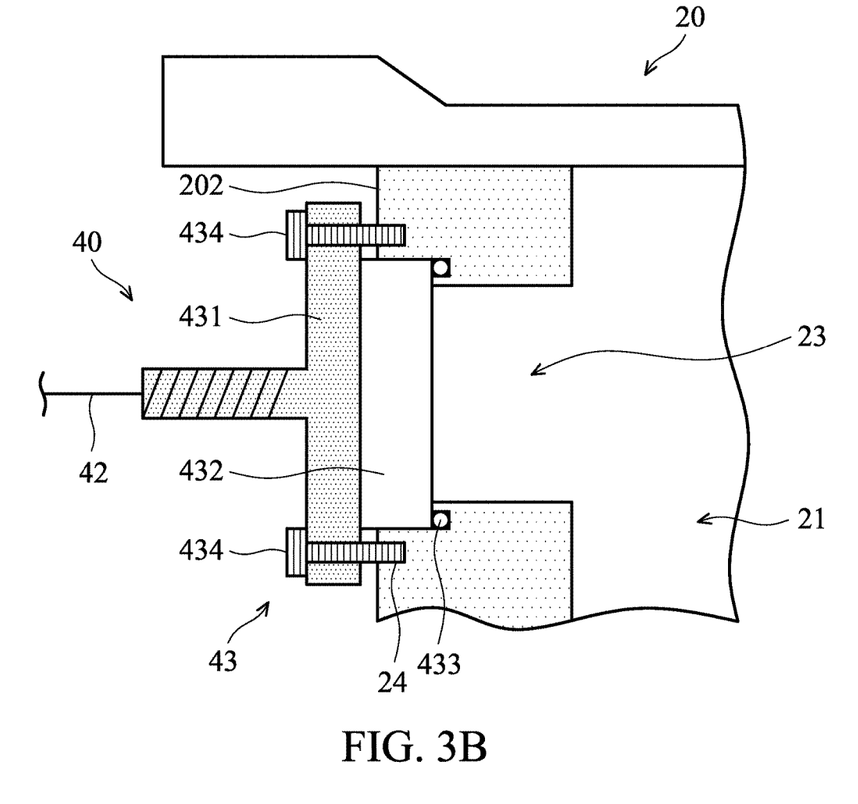
FIG. 3B is a cross-sectional view of a detection module being mounted on a gas mixing member, in accordance with some embodiments.

In some embodiments, as shown in FIG. 3B, after the spectrophotometer 431 is fastened on the compound mixing member 20, the sealing member 433 is compressed to deform. As a result, the viewing window 23 of the compound mixing member 20 is sealed, and a leakage of the gas in the flow path 21 is prevented.

In some embodiments, the width of the substrate 432 is greater than that of the viewing window 23. In addition, in the direction perpendicular to the axis M along which the viewing window 23 extends, the width of the spectrophotometer 431 is greater than that of the substrate 432.

Figure 5:
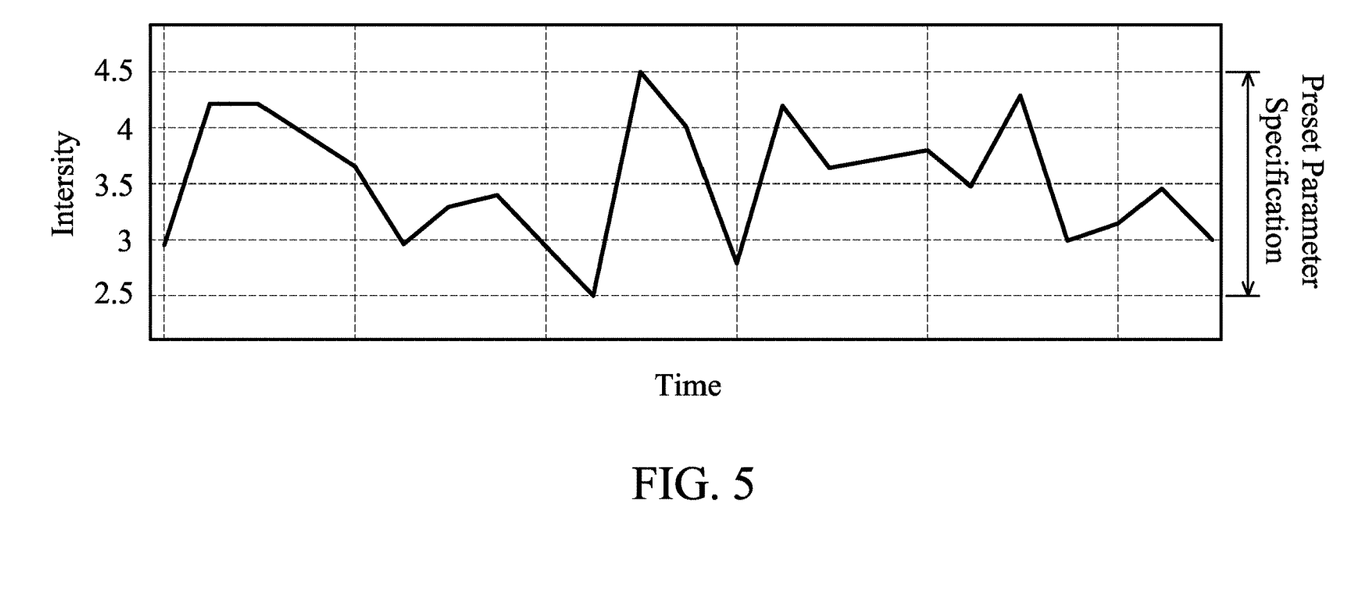
FIG. 5 is a diagram showing the intensity of a spectrum of wavelengths of light in relation to the process time.

The computer 41 is configured to determine the relative intensity of a spectrum of wavelengths of light within the flow path 21. In operation, the plasma 60' passes through the intersection P0 in the flow path 21, and is seen by the spectrophotometer 431 through the viewing window 23. The optical emission spectrometry data acquired is then stored and analyzed in computer 41 and outputs real-time detection results corresponding to the intensity of a spectrum of wavelengths of light within the flow path 21 as shown in FIG. 5.

The control module 50 (see FIG. 1) is configured to control several of the parameters of the processing system 1. In some embodiments, the control module 50 controls the remote plasma module 10 based on an output from the computer 41 of the detection module 40. For example, if the intensity of a spectrum of light wavelengths within the flow path 21 is outside of a preset range, the control module 50 triggers a signal to shut down the remote plasma module 10 and generates a warning signal. As a result, the plasma 60' is stopped from being supplied into the compound mixing member 20, and the operator is asked to perform maintenance on the remote plasma module 10. In some embodiments, the remote plasma module 10 is replaced by another remote plasma module 10 in order to continue to supply the plasma 60' for the plasma process.

Figure 4:
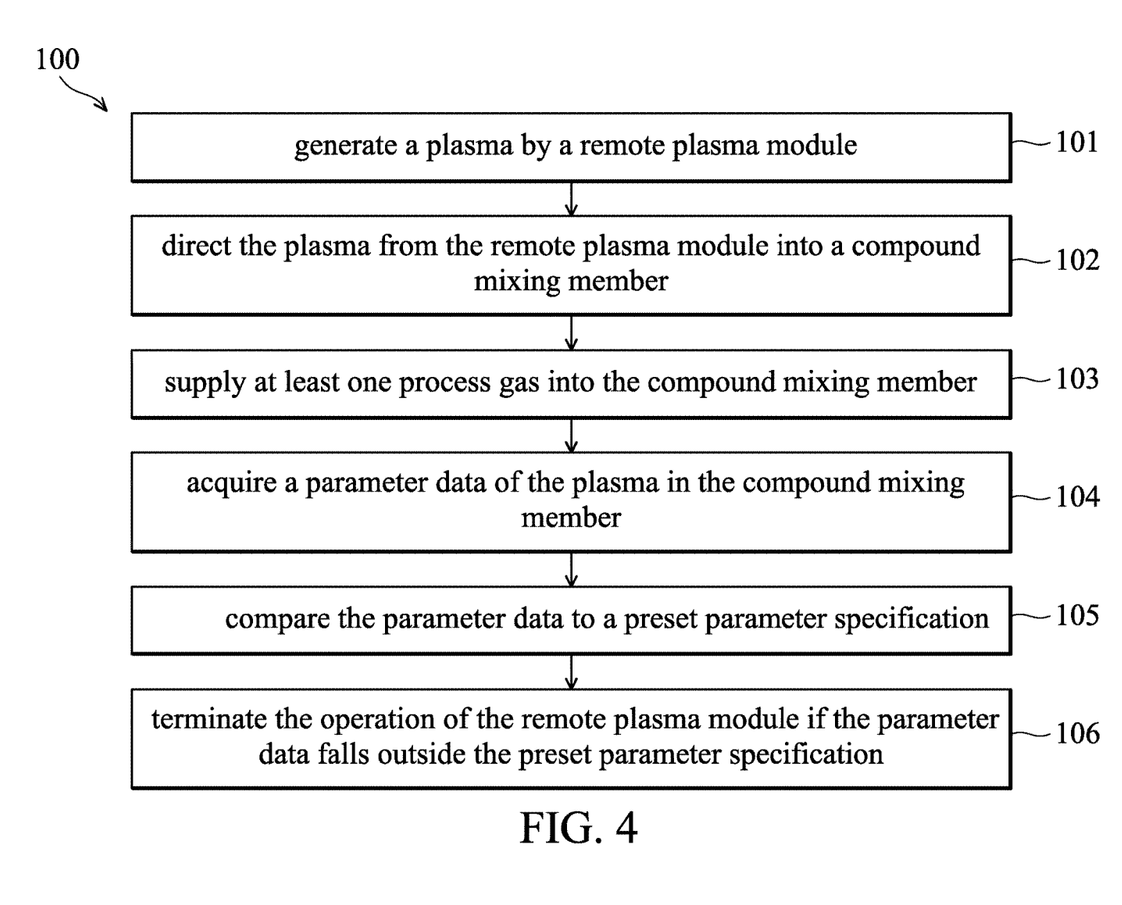
FIG. 4 is a flow chart of a method for supplying plasma material into a processing chamber, in accordance with some embodiments.

FIG. 4 is a flow chart illustrating a method 100 for cleaning a wafer or forming a layer(s) of materials using plasma, in accordance with some embodiments. For illustration, the flow chart will be described along with the schematic views shown in FIGS. 1-3. Some of the stages described can be replaced or eliminated for different embodiments.

The method 100 begins with an operation 101 in which a plasma is generated by a remote plasma module (such as the remote plasma module 10). In some embodiments, the remote plasma module 10 turns the plasma gas 60 (non-plasma phase) from the plasma gas supply unit 71 into plasma 60'. The plasma gas from the plasma gas supply unit 71 may be nitrogen. In some embodiments, the remote plasma module 10 continuously creates the plasma 60' for a preset time period. However, several variations and modifications can be made to embodiments of the disclosure. In some embodiments, for example, the remote plasma module 10 periodically creates plasma 60', and between each individual period, there is no plasma or there is a different plasma excited by other compounds.

In operation 102, the plasma 60' from the remote plasma module 10 is directed into a compound mixing member (such as the compound mixing member 20). In some embodiments, the compound mixing member 20 is positioned outside of the remote plasma module 10 and separated by a distance. The plasma 60' is delivered to the compound mixing member 20 via a gas line 11. The gas line 11 connects the outlet port of the remote plasma module 10 to the inlet port 22 of the compound mixing member 20.

In some embodiments, after being transmitted into the compound mixing member 20, the plasma 60' passes through the flow path 21 in the compound mixing member 20 and flows to processing chamber 30 for a plasma process. The plasma 60' is delivered to the processing chamber 30 via a gas line 12. The gas line 11 connects the outlet port 24 of the remote plasma module 10 to an inlet port of the processing chamber 30. The inlet port of the processing chamber 30 may be directly connected to the showerhead 32 of the processing chamber 30.

In some embodiments, the plasma is transmitted to the processing chamber 30 from the remote plasma module 10 via a conduit. The conduit is constructed by the gas line 11, the flow path 21, and the gas line 12 consequentially. The remote plasma module 10 is connected to an upstream end of the conduit, and the processing chamber 30 is connected to a downstream end of the conduit.

In operation 103, one or more processing gas is supplied into the compound mixing member 20. In some embodiments, the supply of the processing gas and the supply of the plasma or other compound from the remote plasma module 10 are performed simultaneously. For example, the processing gasses 61 and 62 are supplied into the compound mixing member 20 while the plasma 60' or another compound from the remote plasma module 10 is supplied into the compound mixing member 20. Therefore, the processing gasses 61 and 62 and the plasma 60' or the compound are mixed in the flow path 21 of the compound mixing member 20.

However, other variations and modifications can be made to embodiments of the disclosure. In some other embodiments, for example, the supply of the processing gas may start before the plasma 60' is transmitted into the compound mixing member 20. Alternatively, the supply of the processing gas may start after the remote plasma module 10 stops supplying any compound. The plasma 60' from the remote plasma module 10 is not mixed with the other gas or delivered to the processing chamber 30. In some embodiments, the operation 103 is eliminated, and no gas is supplied into the compound mixing member 20.

In operation 104, the parameter data of the plasma 60' in the compound mixing member 20 is acquired by a detection module (such as the detection module 40). In some embodiments, the detection module 40 monitors the plasma 60' by measuring the optical wavelength of the plasma 60' upstream of the flow path 21 formed in the compound mixing member 20. For example, the viewing window 23 through which the detection module 40 sees the plasma 60' directly faces the inlet port 21 used for receiving the plasma 60' from the remote plasma module 10. Since the parameter data of the plasma 60' is acquired before it is mixed with other compounds in the flow path 21, the accuracy of the detection results is improved.

However, the arrangement of the detection module 40 should not be limited to the above embodiments. In some embodiments, for example, the parameter data of the plasma 60' is acquired after the plasma 60' is mixed with other compound in the flow path 21, and the detection module 40 monitors the conditions of a mixture of plasma 60' and the processing gases 61 and 62 in the flow path 21.

In operation 105, the parameter data is compared to a preset parameter specification. In some embodiments, the parameter data is processed by the computer 41 of the detection module 40. The computer 41 may be programmed to interpret parameter data such as the plasma electron density and/or the plasma electron collision rate from the probing assembly 43. In some embodiments, the computer 41 continually compares the parameter data with a preset parameter specification that has been previously programmed into the computer 41, during and/or throughout the plasma process.

In operation 106, the operation of the remote plasma module 10 is terminated if the parameter data falls outside the preset parameter specification. In some embodiments, the measured parameter data drifts outside the upper or lower limit of the specifications, and appropriate data is transmitted to the control module 50, which terminates operation of the remote plasma module 10 or operation of the reaction chamber 32. As a result, failure of the substrate 5 due to being supplied with improper plasma can be avoided. In some embodiments, as shown in FIG. 5, the preset parameter specification is an intensity range of the wavelength detected by the detection module 40. The intensity range is from about 2.5 (a.u.) to about 4.5 (a.u.) in the case of detecting nitrogen plasma gas.

In some embodiments, after operation 105, the remote plasma module 10 is replaced with another remote plasma module 10. Like the original remote plasma module 10, the new remote plasma module 10 is connected to the compound mixing member 20 to supply plasma into the processing chamber 30 for the plasma process. The plasma supplied by the new remote plasma module 10 is also continuously monitored by the detection module 40 to ensure the appropriate processing results of the plasma process performed in the processing chamber.

Embodiments of controlling plasma in a semiconductor fabrication described above use the detection module for real-time monitoring of the plasma supplied by the remote plasma module in the compound mixing member. The remote plasma module stops supplying plasma if the measured plasma parameter data does not remain within the programmed/preset plasma parameter specifications. Therefore, the properties of the plasma process are stabilized. In addition, compared with the conventional method of calculating the etching rate of a film etched by a plasma from a remote plasma module, the disclosed method decreases the risk of failure caused by supplying plasma with the improper density. As a result, the product yield is improved, and the manufacturing cost is decreased.

In accordance with some embodiments, a plasma processing system is provided. The system includes a remote plasma module. The remote plasma module is connected to an upstream end of a conduit and configured to generate a plasma. The system further includes a processing chamber. The processing chamber is connected to a downstream end of the conduit and configured to receive the plasma from the remote plasma module for a plasma process. The system also includes a compound mixing member. The compound mixing member includes a flow path which is constructed as a portion of the conduit. In addition, the system includes a detection module. The detection module is connected to the flow path and configured to monitor at least one parameter of the plasma in the flow path.

In accordance with some embodiments, a plasma processing system is provided. The system includes a remote plasma module configured to generate a plasma. The system further includes a compound mixing member configured to receive the plasma. The system also includes a processing chamber configured to receive the plasma from the compound mixing member for processing. In addition, the system includes a detection module configured to monitor the plasma in the compound mixing member.

In accordance with some embodiments, a method for controlling a plasma in semiconductor fabrication is provided. The method includes generating the plasma by a remote plasma module. The method further includes directing the plasma from the remote plasma module into a compound mixing member. The method also includes acquiring a parameter data of the plasma in the compound mixing member. In addition, the method includes comparing the parameter data to a preset parameter specification. If the parameter data falls outside the preset parameter specification, the operation of the remote plasma module is terminated.

Although the embodiments and their advantages have been described in detail, it should be understood that various changes, substitutions, and alterations can be made herein without departing from the spirit and scope of the embodiments as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the disclosure. Accordingly, the appended claims are intended to include within their scope such processes, machines, manufacture, compositions of matter, means, methods, or steps. In addition, each claim constitutes a separate embodiment, and the combination of various claims and embodiments are within the scope of the disclosure.

What is claimed is:

1. A method for controlling a plasma in semiconductor fabrication, comprising:
   generating the plasma by a remote plasma module;
   providing a compound mixing member connected to the remote plasma module by a line, wherein the compound mixing member includes a main body having a first outer surface and a second outer surface and a first end surface and a second end surface opposing the first end surface, the first end surface and the second end surface connecting the first outer surface and the second outer surface;
   directing the plasma from the remote plasma module through the line extending into the compound mixing member through a first inlet port disposed on the first end surface;
   directing a first processing gas into the compound mixing member through a second inlet port on the second outer surface and directing a second processing gas into the compound mixing member through a third inlet port on the first outer surface, wherein the first processing gas is different than the second processing gas;
   mixing the plasma with the first processing gas at a first point and the second processing gas at a second point in a flow path within a body of the compound mixing member, wherein a distance interposes the first point and the second point, and wherein the second point is further from the first inlet port than the first point by the distance;
   prior to the mixing, acquiring a parameter data of the plasma while in the compound mixing member wherein the acquiring is performed through a window in the second outer surface;
   after acquiring the parameter data, passing the mixed plasma, first processing gas, and second processing gas out of the compound mixing member through an outlet port in the second end surface;
   comparing the parameter data to a preset parameter specification; and
   terminating operation of the remote plasma module if the parameter data falls outside the preset parameter specification and wherein if the parameter data falls inside the preset parameter specification.

2. The method as claimed in claim 1, wherein the parameter data is acquired by measuring optical wavelength of the plasma in the compound mixing member.

3. The method as claimed in claim 1, further comprising replacing the remote plasma module with another remote plasma module after the operation of the remote plasma module is terminated.

4. The method as claimed in claim 1, wherein the plasma is used to form a layer of materials on a semiconductor wafer.

5. The method as claimed in claim 1, wherein the plasma is used to clean a process chamber.

6. The method of claim 1, wherein the providing the compound mixing member includes providing a plurality of holes in the second outer surface; and attaching a spectrophotometer to the second outer surface using a screw mated with each respective hole of the plurality of holes.

7. The method of claim 6, wherein the window is disposed between the plurality of holes.

8. The method of claim 6, wherein the providing the compound mixing member further comprises providing a sealing member adjacent the second outer surface.

9. The method of claim 8 wherein the sealing member is an O-ring.

10. The method of claim 1, wherein the first processing gas is silane ($SiH_4$).

11. The method of claim 10, wherein the second processing gas is Tungsten hexafluoride ($WF_6$).

12. The method of claim 1, the generating the plasma by the remote plasma module includes using a source gas of nitrogen.

13. The method of claim 1, wherein providing the compound mixing member includes in a cross-sectional view of the main body the first outer surface extends linearly from a termination point of the first end surface to a termination point of the second end surface, wherein the second inlet port and the third inlet port are disposed on the linearly extending first outer surface.

14. A method for controlling a plasma in semiconductor fabrication, comprising:
   generating a plasma using a plasma source gas of a first composition;
   directing the generated plasma into a compound mixing member wherein the generated plasma enters the compound mixing member through a first inlet port in the compound mixing member and follows a first flow path within the compound mixing member;

directing a first processing gas into the compound mixing member, the first processing gas entering the compound mixing member through a second inlet port in the compound mixing member, the second inlet port different from the first inlet port and wherein the processing gas follows a second flow path in the compound mixing member separate and different from the first flow path, wherein the first processing gas includes silane;

directing a second processing gas into the compound mixing member, the second processing gas entering the compound mixing member through a third inlet port in the compound mixing member, the third inlet port different from the first and second inlet ports and wherein the second processing gas follows a third flow path in the compound mixing member separate and different from the first flow path, wherein the second processing gas includes tungsten hexafluoride;

providing a detection module having a spectrophotometer and a computer, wherein the spectrophotometer is physically disposed on a first wall of the compound mixing member that is perpendicular a second wall including the first inlet port and is disposed between the first inlet port and the second inlet port, wherein the spectrophotometer physically is disposed on the first wall and includes a sealing member between the spectrophotometer and a window in the compound mixing member;

measuring to acquire a parameter data of the generated plasma in the compound mixing member using the spectrophotometer by measuring the generated plasma through the window, wherein the generated plasma is measured in the first flow path after the generated plasma passes through the first inlet port;

after the measuring, mixing the generated plasma and the first processing gas into a fourth flow path within the compound mixing member;

after mixing the generated plasma and the first processing gas, mixing the generated plasma and first processing gas with the second processing gas;

comparing the parameter data to a preset parameter specification while continuing to direct the generated plasma into the compound mixing member; and terminating an operation of generating plasma if the parameter data falls outside the preset parameter specification.

15. The method as claimed in claim 14, further comprising: providing the mixed generated plasma, the first processing gas, and the second processing gas out of the compound mixing member via an outlet port on a third wall of the compound mixing member, the third wall perpendicular the first wall, wherein after the outlet port the mixed generated plasma and processing gas enters a processing chamber.

16. The method as claimed in claim 14, wherein the parameter data is acquired by measuring optical wavelength of the generated plasma in the compound mixing member.

17. The method as claimed in claim 14, wherein the generating the generated plasma is performed in a remote plasma module, and wherein the terminating the operation of generating the plasma includes terminating the remote plasma module.

18. The method as claimed in claim 14, further comprising: using the generated plasma to form a layer of materials on a semiconductor wafer.

19. The method as claimed in claim 14, further comprising: using the generated plasma to clean a process chamber.

20. The method as claimed in claim 14, wherein the sealing member provides a seal to avoid leakage of the processing gas in the compound mixing member.

* * * * *